United States Patent [19]

Seto

[11] Patent Number: 5,766,868
[45] Date of Patent: Jun. 16, 1998

[54] METHOD OF DETERMINING A VIABLE COUNT USING A HYDROPHOBIC MEMBRANE

[75] Inventor: Susumu Seto, Yokohama, Japan

[73] Assignee: Millipore Corporation, Bedford, Mass.

[21] Appl. No.: 443,654

[22] Filed: May 18, 1995

Related U.S. Application Data

[63] Continuation of Ser. No. 193,680, Feb. 8, 1994, abandoned.

[30] Foreign Application Priority Data

Feb. 10, 1993 [JP] Japan ................... 5-044397

[51] Int. Cl.$^6$ ............... C12Q 1/66; G01N 21/76; B01D 61/00
[52] U.S. Cl. ................ 435/8; 435/4; 435/29; 435/34; 435/259; 435/291.1; 436/172; 436/177; 422/52; 422/82.6; 210/650; 210/651
[58] Field of Search ............... 435/8, 4, 29, 34, 435/259, 291, 311; 436/172, 177; 422/52, 82.05; 210/650, 651

[56] References Cited

U.S. PATENT DOCUMENTS

| | | | |
|---|---|---|---|
| 4,385,113 | 5/1983 | Chappelle et al. | 435/8 |
| 4,618,533 | 10/1986 | Steuck | 428/315.7 |
| 5,258,285 | 11/1993 | Aegidius | 435/8 |
| 5,366,867 | 11/1994 | Kawakami et al. | 435/8 |

FOREIGN PATENT DOCUMENTS

| | | |
|---|---|---|
| 0465987 | 1/1992 | European Pat. Off. |
| 0529084 | 3/1993 | European Pat. Off. |
| 0563858 | 10/1993 | European Pat. Off. |
| 92/14838 | 3/1992 | WIPO |
| 9214838 | 3/1992 | WIPO |

OTHER PUBLICATIONS

Patent Abstracts of Japan –vol. 016 No. 198 (C–0939), 13 May 1992 & JP–A–04 030798.

Tsai et al, *Proc. Soc. Exp. Biol. Med.*, vol. 183, No. 1, pp. 74–80, Oct. 1986.

Seto et al, *Chemical Abstracts*, vol. 118, p. 491, Ref. #208986 p. 1993.

*Primary Examiner*—Cecilia J. Tsang
*Assistant Examiner*—Abdel A. Mohamed
*Attorney, Agent, or Firm*—John Dana Hubbard; Timothy J. King

[57] ABSTRACT

An improved method of determining a viable microbial cell count in a sample solution with an enhanced detection sensitivity is provided, comprising filtering the sample solution through a filtration membrane having hydrophobic properties to entrap microbes within hydrophobic barriers; applying thereto a fine spray of ATP releasing reagent to extract a luminescent ingredient from the microbes; applying thereto another fine spray of liquid luminescence-inducing reagent to allow the released luminescent ingredient to emit luminescence; and measuring the level of the luminescence, using a competent means for measuring the luminescence level. The microbes and the two types of reagents are locally concentrated due to the hydrophobic properties of the membrane and thus the sensitivity is greatly enhanced, permitting instant counting in the case of large microbes, and decreased culture time for smaller bacterial microbes.

16 Claims, 1 Drawing Sheet

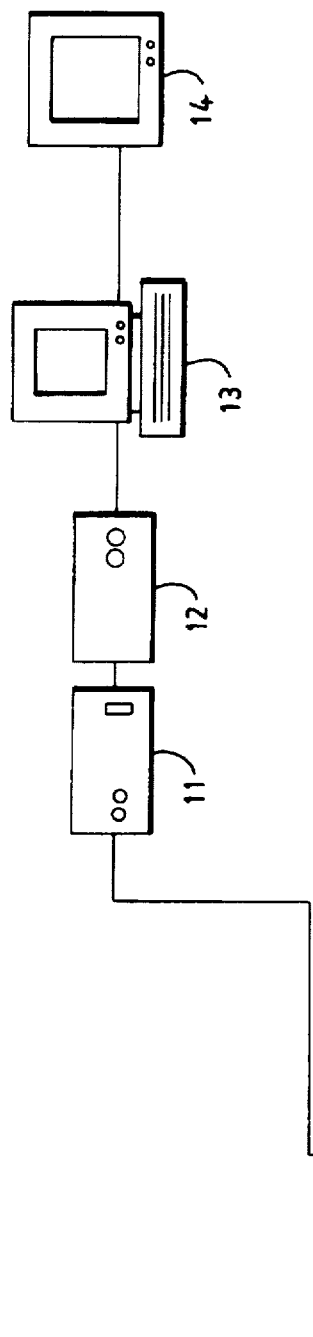
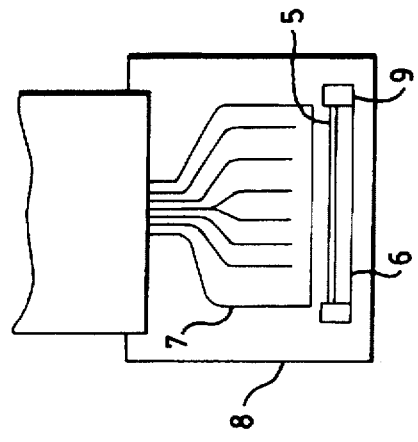
FIG. 1
FIG. 2

METHOD OF DETERMINING A VIABLE COUNT USING A HYDROPHOBIC MEMBRANE

This is a continuation of application Ser. No. 08/193,680 filed on Feb. 8, 1994, now abandoned.

BACKGROUND

1. Field of the Invention

The present invention relates to a rapid, convenient, and highly sensitive method of determining a viable count or number of viable microbes in industrial water, raw materials, intermediates, and products processed in the food and beverage, pharmaceutical, cosmetic and microelectronic industries.

2. Description of the Prior Art

In various industrial applications, such as food and beverage and pharmaceutical, it is well-known that controlling viable microbes in industrial water, raw materials, intermediates, and products is of extreme importance. Quality control of industrial water is also a matter of utmost concern in the electronics industry, and numbers of viable microbes in the water must be monitored at every stage of processing, consequently, determining the viable count is an essential requirement in these industries.

In order to determine a viable count, a conventional, so-called "standard agar plate" method prescribed under Food Hygiene Testing Guide is generally employed. This process, however, is rather cumbersome, and, moreover, requires much time for obtaining the results, causing a significant delay in judgment on the existence of microbes or the number thereof. This delay impacts the production and/or shipment steps, thus causing a considerable loss of time and space. Accordingly, there has been a need in these industries to develop a more rapid and convenient method.

In an attempt to meet this need, a variety of methods for rapid detection have been proposed, among which involve a bioluminescence method (see Japanese Patent Application Kokai Nos. 2-57,197 and 2-163,098, and Haruta, M.: "Facilitation, Automatization, and Acceleration of Food Microbial Testing (orig. in Japanese)", Science Forum, pp.58, Japan (1985). In this method, a small volume of sample solution is collected in a small test tube in the case of solutions having a sufficiently large viable count, or, in the case of a smaller count, the sample solution is filtered through a filter to entrap and concentrate the microbial population thereon. This step is followed by removing the filtration membrane, immersing it in a small volume of, for example, sterile water to suspend the microbes therein, and then taking a portion of the resulting suspension into a small test tube. A releasing reagent is then added to the test tube with a luminescence-inducing reagent to determine the count of adenosine triphosphate (hereinafter referred to as "ATP") contained in the microbes, through use of a luminometer, whereby the viable count is calculated. When the sample solution has an extremely small viable count (e.g., from $10^3$ to $10^4$ cells/ml), however, detection of ATP is impossible in these processes because the ATP level is below the lower limit of determination luminometers. In such case, some time-consuming techniques are required, wherein, for example, the membrane filter element with microbes in the sample solution entrapped is subjected to cultivation in a medium containing nutrients suitable for the microbial growth to increase the viable count above the limit of detection. This fact constitutes a major drawback in the bioluminescence method, thus making further improvement inevitable.

On the other hand, there is another method for determining a viable count, wherein microbes are filtered and entrapped within latticed sections of a filtration membrane, the lattices being made by printing a solution of non-wettable hydrocarbon waxes, Vaseline, silicone waxes or oils, epoxy resins, or polytetrafluoroethylene or polystyrene resins in the shape of square, rectangle, or circle on the membrane. The membrane is then subjected to culturing, for example, at 30° C. for 24 hours, to form microbial colonies within the sections in the manner to avoid any overlapping of colonies, followed by producing optically high contrast between the colonies and the surface of the filtration membrane to automatically count the colonies only (see U.S. Pat. No. 3,929,583). Though the above method is suitable for the purpose of cultivating viable microbes for a sufficient time period to bring their population up to a colony forming level, this method suffers from a reduction in counting efficiency when employed for the purpose of such rapid determination because the extracted luminescent ingredient is diluted to a level below the detectable limit due to an overflow or diffusion of the ingredient into adjacent sections on the membrane surface.

Japanese laid-open patent application number 4-30,798 (published on Feb. 3, 1992) discloses a method and apparatus for counting living microbes by the detection of ATP released from filtered cells. The method involves filtering a microbe-containing solution such that the microbes are retained thereon, contacting the filter with a cell-lysing and light-emitting solution, and then measuring the image signals with a two dimensional photon detecting means thereby obtaining the number of adhered living microbes. No actual examples are described, nor are any details concerning the membrane filter provided, however. Also, there is no disclosure in this application of avoiding dilution of the ATP-containing signal solutions.

In an attempt to solve these problems, an improved method of determining a viable count is described in PCT International Publication No. WO 92/14838, commonly assigned with the present application. In that application, a filtration membrane element is specially prepared, such that a number of small hydrophilic filtration membrane sections are bounded by a plurality of hydrophobic partitions formed on the membrane surface as a rectangular grid. As disclosed in the PCT application, the hydrophobic partitions are formed to penetrate the entire thickness of the membrane element and thus create an effective barrier preventing movement of extracted microbial ingredients and reagents between adjacent hydrophilic membrane sections. The method carried out comprises the steps of entrapping viable microbes contained in a sample solution within the above hydrophilic sections by filtering the solution therethrough; drying the membrane, and then applying reagents for releasing ATP and inducing luminescence to the membrane, using a fine spray; and processing the obtained preparation in a high sensitivity bioluminescence image analysis system to image bright spots originated only from the viable microbes. The filtration membrane, having micropores with pore size of, for example, 0.1 to 1 µm, is made of hydrophilic plastic materials, such as hydrophilic forms of polytetrafluoro ethylene, poly(vinylidene difluoride), polycarbonate, polysulfone and polyamide, or cellulosic materials, such as acetyl cellulose, nitrocellulose and mixtures thereof. The filtration membrane sections, having an area as small as possible, for example, less than 2 mm$^2$ and practically 0.25–1 mm$^2$, are completely or substantially isolated from each other by the hydrophobic partitions, which are made of polyfluoroethylene, poly(vinylidene difluoride), polycarbonate, polyethylene, polypropylene and the like. The partitions have a height above the surface of the membrane of, for example, 0.01 to 0.05 mm. and a width of, for example, 0.1 to 2 mm. The fine spray of the reagents is applied in the required minimum amount so far as it enables the filtration membrane of each section to be wetted, i.e., such an amount as allows the released luminescent ingredient to be diluted and to diffuse at the minimum degree within each section, while being prevented from diffusing and overflowing outside it. In this manner, the luminescence level of each bright spot is elevated thereby increasing detection efficiency, so that rapid determination of a viable count is attained without cultivation of microbes or with just a short cultivation.

Also, localizing the luminescent ingredient enhances detection and determination of a viable count conveniently and accurately for a sample solution with an extremely small viable count. An additional method is described in Japanese Patent Application Kokai No. 4-105,299 filed on Apr. 1, 1992, commonly assigned with the present application, to accelerate the luminescence-inducing reaction, resulting in an elevated luminescence level, wherein the same filtration membrane element as described in the above mentioned publication WO 92/14838 is used to filter a sample solution having a viable count less than 100 cells/element, preferably less than 50 cells/element. A fine spray of an improved ATP releasing agent, i.e., a volatile releasing agent having boiling point below 120° C., is applied to the microbes dispersedly entrapped on the filtration membrane. The releasing agent is then evaporated off rapidly, and thereafter another fine spray of a higher concentration of luminescence-inducing reagent of luciferinluciferase type is applied. In carrying out such a method, wherein ATP release and luminescence reaction takes place in the vicinity of the location where an extremely small amount of both releasing agent and luminescence-inducing reagent exist along with viable microbes, allows the luminescent ingredient to emit luminescence in the immediate vicinity of the microbial location, thus enabling to image the bright spots and to process and analyze the image core effectively using the above bioluminescence image analysis system.

The inventions described in PCT International Publication WO 92/14838 and Japanese laid-open Application No. 4-105,299 have advanced the art by creating more readily distinguishable point sources of light thereby eliminating problems attributed to diffusion of the luminescent signal and have provided accurate measurement of viable microbes in intended applications. Nonetheless, there is still room for improvement particularly in those applications where the level of ATP released is small. It would also be desirable to be able to implement the methods described in the aforesaid patent applications with "off the shelf" membrane filters as opposed to specifically manufactured gridded membranes.

For example, in the food industry these problems are not serious with respect to detecting or counting yeast, which contains a relatively large amount of ATP per cell among a variety of microbes possibly contained in the intermediates or products, i.e., beers and liquors. However, when bacteria, which contain an amount of ATP as small as one tenth to one hundredth of that of yeast ATP, are to be detected or counted, the problems become serious, since it is sometimes impossible to distinguish between the bright spots which originate from viable microbes (bacteria) and those from the background (noise luminescence) which arise from the separation membrane itself where the bacteria are entrapped through filtration or from the sample solution. In such a case, one must select the optimal releasing agent to be used after filtering the practical solution, and spraying conditions (apparatus, particle size, duration, and temperature of the fine spray, etc.), as well as conditions of evaporating the releasing agent, and of adjustment, concentration, spraying and drying of the luminescence-inducing reagent. Further it is necessary to reduce the occurrence of operational noises, to eliminate the noises and to process the desired signals over a certain threshold. More effectively, the filtration membrane retaining bacteria attached thereon should be placed on a vat, which has been impregnated with a medium, preferably a suitable agar medium for the particular bacterial species, and after cultivation at 25° C. to 37° C. for 4 to 15 hours to allow the microbes to proliferate. Release of ATP and inducement of luminescence should be carried out in the immediate vicinity of the location of microbes entrapped on the filtration membrane, followed by detecting and counting the microbes using a bioluminescence image analysis system.

Thus, the inventor has investigated and found an alternative way to more accurately and conveniently detect and count viable microbes, especially bacteria, possibly existing in a sample practical solution.

SUMMARY OF THE INVENTION

The inventor has found that this process leads to an unexpectedly satisfactory result, wherein, under specific conditions, a hydrophobic filtration membrane is used under conditions to contain and confine the individual microbes or colony forming unit on the surface of the membrane to thereby allow individual detection of the suspected microbes. The method according to the present invention allows a significant increase in the detection sensitivity, and provides a means to detect microbes, especially bacteria, as bright spots (point sources) representing their existence individually (i.e. without cultivation), or as a colony forming unit formed after cultivation of bacteria after filtration.

The present method also further enhances the effect, when the concentration of luminescence-inducing reagent used is elevated twice to tenfold compared with those usually used to increase the rate of luminescence, thereby increasing the luminance of the bright spots.

The present method is based on a principle that applying a fine spray of a liquid releasing reagent and a subsequent liquid luminescence-inducing reagent to a hydrophobic filtration membrane allows the ultrafine microparticles of these reagents to be attached thereto at the exact point of microbial existence, and allows the released luminescent ingredient to emit luminescence without any dilution or diffusion. In a first embodiment, to attach the viable microbes in a sample solution onto a flat hydrophobic filtration membrane, the membrane is wetted with a hydrophilic solvent such as alcohol followed by washing it with water, and thereafter the sample solution is filtered through the membrane using, for example, vacuum filtration to entrap the microbes, followed by drying.

Then, the hydrophilic solvent is evaporated off and the membrane becomes hydrophobic. Alternatively, the hydrophobic filtration membrane is treated with a solution of hydrophilic polymers, such as poly(vinyl alcohol) and poly (vinylpyrrolidone), and thereafter the sample solution is filtered, enabling the membrane to entrap the microbes on the one hand, and to resume to be hydrophobic through the washing effect of the solution being filtered which removes the hydrophilic polymers on the other hand.

When the releasing reagent for the luminescent ingredient ATP is then applied in a fine spray, the hydrophobic membrane allows the reagent to retain an ultrafine particle size due to its surface tension, and to release the luminescent ingredient from the microbes without any displacement, diffusion or dilution. The releasing reagent may be either a volatile one, such as methanol or ethanol, or a non-volatile one such as a surfactant. The luminescence-inducing reagent also retains its particle size due to its surface tension, and induces luminescence of the luminescent ingredient from viable microbes without any displacement, diffusion or dilution. If the luminescence-inducing reagent is used in an elevated concentration, the increased rate of induction of luminescence will cause an increased luminescence of the bright spots, thus resulting in an enhanced detection efficiency as contrasted with background noise luminescence. Further, even an extremely low level of luminescence can be detected and counted by using a high-sensitivity luminescence image analysis system. Employment of the present invention will drastically reduce the time and trouble as required in conventional methods for cultivation of microbes even in case of detecting bacteria in a sample solution with higher noise luminescence, and permits rapid counteraction of the bacterial contamination due to immediate availability of the results, thus providing an economically beneficial effect.

The invention is directed to a method of determining the number of living microrganisms in a sample solution suspected of containing same, comprising: filtering the sample solution through a hydrohobic filtration membrane thereby entrapping said microbes thereon within hydrophobic barriers; spraying a solution of an ATP releasing reagent on said microbe-containing membrane to release ATP from the microbes contained within the hydrophobic barriers; spraying a solution of a luminescence-inducing reagent on the membrane to induce luminescence; and measuring the level of said luminescence, using means for measuring said luminescence level.

BRIEF DESCRIPTION OF THE DRAWINGS

FIG. 1 is a schematic diagram of a bioluminescence image analysis system to be used according to the present invention.

FIG. 2 is an enlarged partial view of FIG. 1.

DETAILED DESCRIPTION OF THE INVENTION

In the following, a further detailed description of the present invention will be given. In a preferred embodiment the hydrophobic filtration membrane is made of a commonly known hydrophobic material, such as, poly(vinylidene fluoride) (PVDF), polytetrafluoroethylene (PTFE) or polyethylene (PE), or of a relatively hydrophobic hydrophilic material, such as polycarbonate (PC), polypropylene (PP), polyamide (PA), polysulfone (PS) or polyether sulfone. Preferably, these materials exhibit minimum background luminescence. As used herein, the term "hydrophobic filtration membrane" refers to those membranes which, when a fine spray is applied, retain the reagents in a fine droplet form, and which substantially do not absorb the reagents. The hydrophobic filtration membrane may be produced by any means for forming micropores in a sheet selected from any hydrophobic materials. For example, the micropores may be formed by directing an electron beam to the sheet. Preferably, the hydrophobic filtration membrane may be treated with a hydrophilic material such as polyvinylpyrrolidone to impart a hydrophilic nature to the membrane, which is easily washed out when a liquid which contains microbes is filtered with thusly treated membrane.

The detectable number of viable microbes in a sample solution to be entrapped on the filtration membrane 1 according to the present invention, may be usually less than 100 cells/membrane, often less than 50 cells, and possibly less than 20 cells/membrane. To entrap viable microbes contained in a sample solution on said filtration membrane, various processes may optionally be employed, including those wherein the hydrophobic membrane is temporarily allowed to be hydrophilic, then subjected to vacuum filtration of the sample solution, and thereafter dried to resume its hydrophobicity. However, the microbes themselves should remain hydrophilic. Those microbes which can effectively be detected using the method according to the present invention include any microorganisms, especially bacteria and molds. Molds can be detected with relative ease, and, in most cases, bacteria also can be detected by directly applying the method according to the present invention. In some cases, it might be necessary to cultivate the microbes. In such cases, however, the time period for cultivation can be reduced, as compared with the method described in the above PCT International Pubication WO 92/14,838. The luminescent ingredient which can be released from the microbes is adenosine triphosphate (ATP).

Liquid releasing reagents for the luminescent ingredient, ATP, include alcohols, ethers, esters, and halogenated derivatives of methane, ethane, or ethylene, as well as acetonitrile, triethylamine and others. Releasing agents which have a boiling point equal to or below 120° C. and can readily be evaporated off are especially preferable. Residual releasing agents, for instance a surfactant, also release ATP, but will indirectly exert an inhibitory effect on the luminescence-inducing enzyme by not destroying ATPases like the alcohol extracting reagent would.

The luminescence inducing reagent, a composition of luciferin and luciferase, is preferably used in a concentration increased twice to ten times, particularly three to six times, of the standard concentration. By using an increased concentration of the reagent, the rate of luminescent reaction is accelerated, resulting in an increase both in the luminescence level of the bright spots and in the speed of detection. The term "standard concentration" as used herein is defined as those specified for regular use of conventional luminescence-inducing reagents (for example, Lucifer LU™, a reagent of luciferin/luciferase type from Kikkoman Co., Ltd.). In the case of Kikkoman luminescence-inducing reagent, a standard solution consists of 70 mg of freeze dried product which contains 0.15 mg of luciferine and 0.1 mm of luciferase and is reconstituted in 5 ml of water.

Preferably, these liquid reagents are applied in a fine spray, i.e. a mist-like spray of fine particles or droplets having a size of 20 μm or less, preferably from 5 to 10 μm. As the means for generating such a spray, ultrasonic fine-particle sprayers, especially automatic ones are desired. It is important not to wet the hydrophobic membrane completely, because these situations lead to diffusion of the luminescent components out of their respective restricted areas with the concomitant loss in the ability to detect the point sources of light emanating from individual microbes.

According to the invention, it is possible to allow ATP to exist with a high concentration at locations very close to the points of entrapping of microbes owing to the large surface tension of the ATP containing solution with respect to the hydrophobic membrane. Further, fine droplets of the luminescence-inducing reagent having a concentration of from about 2–10 times and preferably from about 3–6 times as high as the standard concentration are placed on the hydrophobic membrane which retains the ATP in a condition such that the diffusion is restricted. Accordingly, the luminescent level of the spots is increased and the sensitivity of detection is increased almost ten times as high as compared to the methods using a hydrophilic membrane.

Employing the procedures outlined above allows detection of ATP in the amount in the order of 1 fg (femtogram).

In a preferred embodiment of the method of the invention, a sample solution is filtered using a filtration apparatus, which is a cup-shaped vessel, such as Milliflex Filter Unit (brand name Sterifil™) available from Nippon Millipore Co., Ltd., with the above hydrophobic filtration membrane having been mounted on to entrap viable microbes in the solution thereon. The hydrophobic filtration membrane is then removed from the apparatus, dried up, and thereafter mounted on a preparation holder to be subjected to a gentle fine spray of the ATP releasing reagent, for example, NBR™TM from Lumac Co., Ltd., onto the membrane for 10 seconds, using an ultrasonic sprayer (available from Matsushita Electric, Industry Co., Ltd.). After 20 seconds, the membrane is subjected to another gentle fine spray of a luciferin-luciferase luminescence-inducing reagent (LumitPM™, Lumac Co., Ltd.) for 10 seconds, using the same sprayer as above, to induce bioluminescence. Subsequently, the filtration membrane which has been prepared to emit luminescence (hereafter referred to as "preparation") is placed on a preparation holder, and, after being covered with a total reflection plate, the point source bright spots are counted to determine the viable count. This determination is made by means of a bioluminescence image analysis system (for example, ARGUS-50/CL(tradename), Hamamatsu Photonics Co., Ltd.) of a tapered-fiber input type, wherein an image processing is carried out after the accumulation of luminescence for a time period of, for example, two minutes, then a further image processing is carried out to erase any luminescence to be considered as background noise, and finally the remaining bright spots are counted. The bioluminescence analysis system to be used herein is a novel and innovative device, which can detect with high sensitivity even such faint luminescence as could hardly be detected by conventional instruments, and significantly intensify the signal for processing. Furthermore, the processing and analysis are carried out more rapidly and conveniently. When combined with the effects caused by the fine sprays using the sprayer of particular reagents onto the hydrophobic filtration membrane according to the present invention, the system enables detection of even a single microbial cell, contributing to provide an extremely excellent method of determining a viable count. The outline of the system is as shown in FIGS. 1 and 2. This system comprises a preparation holder 9 for supporting the filtration membrane (preparation) 5, which has been treated with the releasing and luminescence-inducing reagents as stated above; a total reflection plate 6; a housing for shading 8; tapered fibers 7 juxtaposed as closely as possible to the filtration membrane for detecting the luminescence in a two-dimensional mode; an ultrahigh-sensitivity TV camera 10 consisting of a photoamplifier component and a camera to be; a camera controller 11; an image processor 12; a data analysis device 13; and a monitor TV 14. ARGUS-50/CL™ of tapered-fiber input type from Hamamatsu Photonics, Co., Ltd., or those components having an equivalent performance of measurement. As the ultrahigh-sensitivity TV camera 10, a TV camera equipped with cooled solid-state camera device (CCD) may be employed, in which the CCD is cooled to a temperature from about −30° C. to −120° C. to restrain the background noise from the camera itself, enabling the camera to detect faint light. For example, a cooled CCD digital imaging system is available from Hamamatsu Photonics. Alternatively, the system may be operated by inverting the relative position of tapered fibers 7 in the camera tube component to the ultrahighsensitivity TV camera 10, and placing the preparation holder 9, with a preparation (membrane 5) mounted thereon, on the tapered fibers 7. Desirably, the preparation 5 may be placed as closely as possible to the tapered fibers 7, thereby to significantly enhance the sensitivity of measurement and to eliminate the conventional necessity of scanning. For the purpose of automatic counting, if desired, sprayer(s) for releasing and luminescence-inducing reagents, and other associated equipment such as preparation carrier may be arranged in a set.

To determine the viable count, the preparation holder 9 bearing a preparation (the filtration membrane retaining microbes to be counted) after the above mentioned luminescence-inducing process is placed on the surface of the tapered fibers 7 in close contact therewith. Using the ultrahigh-sensitivity TV camera 10, the camera controller 11, and the image processor 12, the photons emitted from the preparation 5 are accumulated for 30 to 180 seconds, such as 120 seconds, in a two-dimensional mode to pick up an image of the luminescence from microbial bodies, which is then processed with the data analysis device 13 to be displayed on the monitor TV 14, with bright luminescence originated from viable microbes only remaining and faint noise luminescence having been erased. Any luminescence originating from other than the microbial bodies are erased by this processing, resulting in substantial correspondence between the number of the bright spots detected and the viable count.

In the most preferred embodiment on the present invention, the ingredient to be extracted from viable microbes is adenosine triphosphate (ATP). In this case, the extracting reagent is that for ATP (for example, NRB™from Lumac), which is applied in a fine spray, using a sprayer (for example, Ultrasonic Aspirator™from Matsushita Electric Inc.), for extracting ATP from microbes entrapped in the filtration membrane. A luminescence-inducing reagent (for example, Lumit-PM from Lumac Co.) is then applied in a similar manner, for inducing luminescence. As stated above, the preparation thus obtained is then subjected to the above bioluminescence image analysis system, in which the luminescence is accumulated for 30 to 180 seconds, and thereafter only bright spots having luminescence higher than that of background luminescence are left in the monitor TV and displayed thereon. This means that a bright spot displayed on the TV monitor directly represents the existence of a microbial cell, since any bright spots having a lumiescence equal to or below the threshold luminescence are erased from the screen of the monitor TV. The threshold luminescence is defined as the highest luminescence of a preparation which has been obtained from sterilizing an aliquot of the sample solution and inducing luminescence by the same treatment as done to the testing sample.

In the preferred embodiment of the present invention viable microbes are entrapped on a hydrophobic filtration membrane. Subsequent application of a suitable amount each of an ATP extracting solution and a solution of luminescence-inducing reagent (particularly a luciferin-luciferase reagent) in a fine spray enables the applied particles of reagents to retain their particulate forms by virtue of their intrinsic surface tension without any diffusion, displacement, or dilution. This allows the luminescent ingredient in the microbes to be retained in place in a relatively higher concentration after luminescence induction, enabling one to readily measure an extremely small amount of the ingredient.

Moreover, the bioluminescence image analysis system according to the present invention, to which the preparation (filtration membrane) is subjected after luminescence induction, enables detection of even very faint luminescence from a single microbial cell in a two-dimensional mode, thus making it possible to determine the viable count, even if it should be an extremely small number, automatically, rapidly, and conveniently, and with a high sensitivity. In other words, employment of a TV camera, consisting of tapered fibers, photoamplifier component, and imaging tube, has enabled the indication (recognition) of the luminescence originated from viable microbes as very bright spots, so that any noise luminescence from other materials than viable microbes can readily be eliminated by comparing it with a threshold luminescence obtained from a sterilized sample solution, thereby enabling the determination of the viable count, even if it should be an extremely small number (for example, several cells/100 ml of sample solution) automatically, as well as rapidly and conveniently. In addition, it may sometimes be important to detect only one microbial cell present in a sample solution, as is the case of coliform test for foods and cooling beverages.

It is preferred, in the case of testing bacteria, to place a hydrophobic filtration membrane, with microbes (bacteria) having been entrapped by filtering the sample solution, on a pad or a nutrient agar plate containing the most suitable nutrients for their growth, to cultivate them for a short time period (for example, less than three hours), thereby increasing the viable count by forming colonies of microbes within the same sections, and thereafter to subject the filtration membrane to determination. Employing such a procedure enables one to obtain significantly luminous bright spots, providing means for more accurate determination.

Cited as one example of the most preferred hydrophobic filtration membranes is a polycarbonate filtration film (e.g. 0.4 μm ISOPORE™, sold by Millipore Corp.) having pores of very uniform diameter which has been treated with a water-soluble hydrophilic polymer such as polyvinyl pyrrolidone to make the surface of the hydrophobic polycarbonate membrane hydrophilic. The hydrophilic film is easily washed away when the liquid containing microbes is filtered through the filtration membrane thereby returning said membrane to its original hydrophobic state.

Having now described the invention, the same will be further illustrated by the following non-limiting examples.

EXAMPLES

Example 1

A series of 0.5 μl of aqueous ATP solutions each containing ATP in the amount of $10^{-12}$ g, $5 \times 10^{-13}$ g, or $5 \times 10^{-14}$ g,-were prepared. Hydrophobic filtration membranes according to the present invention (HVHP, manufactured by Nippon Millipore Limited) were spotted with one of the above solutions, air-dried, and then subject to a fine spray of a luminescence-inducing reagent (Lucifer-LU from Kikkoman Co., Ltd.), using a pressurized sprayer (from Shin'ei Kogyo Co.), to induce luminescence. Immediately after luminescence was induced, the filtration membranes were placed into a bioluminescence image analysis system (RMDS from Nippon Millipore Limited), and the luminescence level of the bright spots were measured. The results obtained are shown in Table 1. For comparison, the same procedure as above was followed, using hydrophilic gridded filtration membranes (HVWP from Nippon Millipore Limited) instead of HVHP. The results are also shown in Table 1.

TABLE 1

| ATP | HVHP | HVWP |
|---|---|---|
| $10^{-12}$ | 28,860* | 20,940* |
| $5 \times 10^{-13}$ | 21,930 | 17,270 |
| $10^{-13}$ | 6,020 | 3,530 |
| $5 \times 10^{-14}$ | 2,410 | 620 |

*Luminescence level defined by the number of photons emitted from a bright spot consisting of 25 × 25 pixels among 250,000 pixels on the screen of the monitor.

As indicated in Table 1, the sensitivity of detection of ATP is higher when detected on HVHP. Luminescence level is higher at the lower ATP concentration.

Example 2

A series of 0.5 μl of aqueous ATP solutions each containing ATP in the amount of $5 \times 10^{-13}$ g, $5 \times 10^{-14}$ g, or $2 \times 10^{-14}$ g were prepared. Hydrophobic filtration membranes (HVHP) were spotted with one of the above solutions, and air-dried. A solution of luminescence-inducing reagent (Lucifer-LU) of five-fold concentration was prepared by dissolving the reagent in 1 ml, i.e., one fifth of the prescribed volume, of the solvent of the reagent. Induction of luminescence and measurement of the luminescence level were carried out as in Example 1. For comparison, the same procedure as above was followed, using the luminescence-inducing reagent of standard concentration instead of the increased one. The results of these experiments are shown in Table 2.

TABLE 2

| Concentration of the Luminescence-Inducing Reagent | | |
|---|---|---|
| ATP | 5-fold | standard |
| $5 \times 10^{-12}$ | 22,050* | 17,375* |
| $5 \times 10^{-14}$ | 2,320 | 710 |
| $2 \times 10^{-14}$ | 1,970 | 50 |

*luminescence level emitted from the monitor screen (25 × 25 pixel area).

Table 2 illustrates the increased sensitivity of detection of ATP by use of 5-fold concentration of luminescence inducing reagent.

Example 3

A platinum loop of Escherichia coli (IFO 13898) was inoculated into a test tube containing 5 ml of SCD medium (Nippon Pharmaceutical Co., Ltd.), and cultivated at 37° C. overnight. The medium was diluted with HEPES buffer solution (pH 7.75, Sigma Co.), so that a sample solution containing about 100 CFU/ml of bacteria was prepared.

After a hydrophobic membrane made of PVDF (HVHP, 47 mm diameter, Nihon Millipore Limited) was mounted to a filtration apparatus (Milliflex Filter Unit, Nihon Millipore Co., Ltd.), the membrane was impregnated with a small amount of methanol to make it hydrophilic, washed thoroughly with water, and 10 ml of HEPES buffer solution and 0.2 ml of the above sample solution were poured on the membrane successively for a suction filtration. After washing with 15 ml of HEPES buffer solution in three times, the filtration membrane was removed from the apparatus, air-dried, and mounted on a preparation holder. The membrane was then subjected to a particulate spray of methanol for 30 seconds, using a pressurized sprayer (Shin'ei Kogyo Co.), and, after standing for 5 minutes to evaporate methanol off, the membrane was subjected to another particulate spray of luminescence-inducing reagent with five-fold concentration as used in Example 2 to induce luminescence.

Immediately after the spray, photons were accumulated for two minutes using the same bioluminescence image analysis system as used in the preceding Examples, noise luminescence was subtracted, the bright spots imaged on the monitor TV were measured for their luminescence level to contain results as shown in Table 3. For comparison, 0.2 ml of the same sample solution were spread on a SCD agar plate (Nippon Pharmaceutical Co., Ltd.), and cultivated at 37° C. for 48 hours. Measurement was then carried out on the colonies formed, to obtain results as also shown in Table 3.

TABLE 3

| Exp. No. | Hydrophobic Membrane (bright spots/membrane) | Agar Plate Method (CFU/0.2 ml) |
| --- | --- | --- |
| 1 | 22 | 18 |
| 2 | 19 | 23 |
| 3 | 16 | 19 |

Table 3 indicates a good correlation between the two methods of detection.

Example 4

In a similar manner as in Example 3, Escherichia coli (IFO 13898) was cultivated in 300 ml of commercially available canned beer which had been filtered under sterile condition, and the beer was diluted with HEPES buffer to prepare a sample solution containing about 100 CFU/ml of the bacteria. After a hydrophobic membrane made of PVDF (HVHP, 47 mm diameter, Nippon Millipore Limited) was mounted to a filtration apparatus (Milliflex Filter Unit, Nippon Millipore Co., Ltd.), the membrane was impregnated with a small amount of methanol, washed thoroughly with water, and 0.2 ml of the sample solution were added to the filtration apparatus for a suction filtration. After washing with HEPES buffer, air drying, releasing ATP, and inducing luminescence, as in Example 3, the membrane was subjected to counting the bright spots by the bioluminescence image analysis system to obtain results as shown in Table 4. Also, 0.2 ml of the sample solution were spread on a SCD agar plate and cultivated at 37° C. for 48 hours to carry out the measurement on the colonies formed. Results obtained from both experiments are also shown in Table 4

TABLE 4

| Exp. No. | Hydrophobic Membrane (br. spots/mem.) | Agar Plate (CFU/0.2 ml) |
| --- | --- | --- |
| 1 | 17 | 20 |
| 2 | 15 | 15 |
| 3 | 11 | 12 |

According to the data in Table 4, there is good correlation between the two methods as applied to commercial products (beer) containing *E. coli*.

Example 5

In a manner similar to that of Example 3, Lactobacillus brevis (IFO 3345) was cultivated for overnight in 300 ml of commercially available canned beer which had been filtrated under sterile condition, and the beer was diluted with HEPES buffer to prepare a sample solution containing about 100 CFU/ml of the bacteria. After 0.2 ml of the sample solution were filtered through a polycarbonate membrane (Isopore 0.4, 47 mm diameter, Nippon Millipore Limited), the membrane was placed on a SCD agar plate and cultivated at 30° C. for 8 hours. After air-drying, releasing ATP, and inducing luminescence, as in Example 3, the membrane was subjected to measurement on the bright spots using a bioluminescence image analysis system, to obtain results as shown in Table 5. 0.2 ml of the solution were spread on a SCD agar plate and cultivated at 30° C. for 5 days to count the colonies formed. Results obtained from both experiments are also shown in Table 5.

TABLE 5

| | Hydrophobic membrane | | Agar Plate |
| --- | --- | --- | --- |
| Exp. No. | No.[1] | Lumi.[2] | CFU/0.2 ml |
| 1 | 22 | 541 | 18 |
| 2 | 17 | 494 | 23 |
| 3 | 20 | 612 | 24 |

[1] Number of bright spots/1 membrane.
[2] Average luminance: Photons from each spot consisting of 25 × 25 pixels were totaled over the screen and divided by the total number of the spots.

This example shows good correlation beween the hydrophobic membrane and the conventional detection method of lactobacillus brevis in beer.

The present invention provides the following advantageous effects.

(1) In the method according to the present invention, a higher sensitivity is attained than in the method using a standard agar plate, resulting in an easier detection of luminescence (see Table 3).

(2) In the method according to the present invention, an increased concentration of luminescence-inducing reagent may be used to obtain an enhanced level of luminescence, so that a luminescence exceeding the lower limit of detection in conventional methods is attained, also resulting in an easier detection of luminescence (see Table 2).

(3) In the method according to the present invention, sample solutions can be tested without necessitating cultivation completely or for more than a short time period, resulting in an immediate or rapid determination (see Tables 3–5).

Though the present invention is heretofore described referring to the drawings and examples, which are given here for illustrative purposes only, the spirit and scope of the present invention is limited only by the attached claims.

We claim:

1. A method of determining an approximate number of living microorganisms in a sample solution, comprising the steps of:

(a) filtering said sample solution through a hydrophobic filtration membrane thereby entrapping any living microorganisms in the sample solution on an outer surface of said hydrophobic membrane;

(b) spraying an adenosine triphosphate releasing reagent onto said hydrophobic membrane to form droplets at the outer surface, whereby each droplet that contacts a microorganism releases adenosine triphosphate from said microorganism, each of said droplets that contacts a microorganism thereby causing formation of a localized deposit of the released adenosine triphosphate;

(c) spraying a solution of a luminescence-inducing reagent onto said membrane to induce luminescence of each localized deposit of adenosine triphosphate, thereby forming a luminescent spot at each localized deposit; and (d) identifying the number of luminescent spots, thereby determining the approximate number of living microorganisms in the sample.

2. The method of claim 1, wherein said luminescence-inducing reagent comprises luciferin/luciferase.

3. The method of claim 1 wherein said adenosine triphosphate releasing reagent is selected from the group consisting of an alcohol, an ether, an ester, a halogenated derivative of methane, ethane, ethylene, acetonitrile and triethylamine, said reagent having a boiling point equal to or below about 120° C.

4. The method of claim 1, wherein said adenosine triphosphate releasing reagent is methanol.

5. The method of claim 1, wherein said adenosine triphosphate releasing reagent is ethanol.

6. The method of claim 1, wherein said hydrophobic filtration membrane is selected from the group consisting of poly(vinylidene fluoride), polytetrafluoroethylene, polyethylene, polycarbonate, polypropylene, and polysulfone.

7. The method of claim 1, wherein said luminescence is measured with a bioluminescence image analysis system that includes a dark box, tapered fibers, a photoamplification device and an imaging tube.

8. The method of claim 1 wherein said luminescence is measured with a tapered optical fiber-input charged coupled device camera.

9. The method of claim 1, wherein said luminescence-inducing reagent is sprayed in the form of a mist of particles having a size of about 20 μm or less.

10. The method of claim 1, further comprising a step of culturing said hydrophobic membrane to create small colonies on said hydrophobic membrane.

11. The method of claim 1, wherein the sample solution is directed through a hydrophobic membrane filter that is a polycarbonate membrane filter, said solution of adenosine triphosphate releasing agent is a volatilizable alcohol solution, and further including the step of volatilizing said alcohol solution from said polycarbonate membrane filter prior to spraying the luminescence-inducing agent into said membrane filter.

12. The method of claim 1, further including the step of treating said hydrophobic filtration membrane with a hydrophilic agent prior to filtering said sample solution through the filtration membrane.

13. The method of claim 12, further including the step of removing said hydrophilic agent following filtration of said sample solution.

14. The method of claim 13, wherein said hydrophilic agent is removed by volatilizing said hydrophilic agent.

15. A method for obtaining a viable cell count of a sample solution, comprising the steps of:

(a) filtering the sample solution through a hydrophobic polycarbonate membrane filter, thereby entrapping any microorganisms in the sample solution on an outer surface of said hydrophobic polycarbonate membrane filter;

(b) applying a solution of a volatilizable alcohol in a fine spray onto said hydrophobic polycarbonate membrane filter, thereby forming droplets at the outer surface, whereby each droplet that contacts a microorganism releases adenosine triphosphate from said microorganism, said droplets subsequently volatilizing to thereby form at least one localized deposit of the released adenosine triphosphate corresponding to each droplet contacting a microorganism on said hydrophobic membrane;

(c) applying a luciferin-luciferase solution onto said membrane filter as a spray to induce luminescence of each localized deposit of adenosine triphosphate, thereby forming a luminescent spot at each localized deposit; and (d) identifying each luminescent spot, thereby obtaining a viable cell count of the sample solution.

16. The method of claim 15 wherein said hydrophobic polycarbonate membrane filter is contacted with polyvinylpyrrolidone prior to being contacted with said sample solution.

* * * * *